(12) United States Patent
Keltjens et al.

(10) Patent No.: US 7,329,747 B2
(45) Date of Patent: Feb. 12, 2008

(54) SYNTHESIS OF OLANZAPINE AND INTERMEDIATES THEREOF

(75) Inventors: Rolf Keltjens, Nijmegen (NL); Theodorus H. A. Peters, Arnhem (NL)

(73) Assignee: Synthon IP Inc., Gainesville, VA (US)

( * ) Notice: Subject to any disclaimer, the term of this patent is extended or adjusted under 35 U.S.C. 154(b) by 470 days.

(21) Appl. No.: 11/050,850

(22) Filed: Jan. 27, 2005

(65) Prior Publication Data

US 2005/0267099 A1    Dec. 1, 2005

Related U.S. Application Data

(60) Provisional application No. 60/569,607, filed on May 11, 2004, provisional application No. 60/539,120, filed on Jan. 27, 2004.

(51) Int. Cl.
*C07D 487/02* (2006.01)

(52) U.S. Cl. .................................. 540/557

(58) Field of Classification Search ............ 540/557
See application file for complete search history.

(56) References Cited

U.S. PATENT DOCUMENTS

| 4,115,568 | A | 9/1978 | Chakrabarti et al. | 514/220 |
|---|---|---|---|---|
| 5,229,382 | A | 7/1993 | Chakrabarti et al. | 514/220 |
| 5,457,101 | A | 10/1995 | Greenwood et al. | 514/220 |
| 5,605,897 | A | 2/1997 | Beasley, Jr. et al. | 514/220 |
| 5,736,541 | A | 4/1998 | Bunnell et al. | 514/220 |
| 6,063,802 | A | 5/2000 | Winterborn | 514/397 |
| 6,348,458 | B1 | 2/2002 | Hamied et al. | 514/220 |
| 2002/0086993 | A1 | 7/2002 | Davies et al. | 540/495 |
| 2004/0265375 | A1 | 12/2004 | Platteeuw et al. | 424/464 |
| 2005/0272720 | A1 | 12/2005 | Keltjens | 514/220 |
| 2005/0272721 | A1 | 12/2005 | Keltjens | 514/220 |

FOREIGN PATENT DOCUMENTS

| EP | 454436 B1 | 9/1995 |
|---|---|---|
| EP | 733635 B1 | 8/2001 |
| EP | 831098 B1 | 11/2001 |
| EP | 0828494 | 7/2002 |
| WO | WO 98/11893 | 3/1998 |
| WO | WO 99/16313 | 4/1999 |
| WO | WO 01/47933 A1 | 7/2001 |
| WO | WO 02/18390 A1 | 3/2002 |
| WO | WO 03/007912 A2 | 1/2003 |
| WO | WO 03/091260 A1 | 11/2003 |
| WO | WO 03/097650 | 11/2003 |
| WO | WO 03/101997 A1 | 12/2003 |
| WO | WO 2004/000847 A1 | 12/2003 |
| WO | WO 2004/006933 A2 | 1/2004 |

OTHER PUBLICATIONS

"Anhydrates and Hydrates of Olanzapine: Crystallization, Solid-State Characterization, and Structural Relationships", *Crystal Growth & Design*, 2003, vol. 3, No. 6, pp. 897-907.
"Catalytic Transfer Hydrogenation of Aromatic Nitro-compounds", *Chinese Journal of Pharmaceuticals*, 2001, 32(9), pp. 391-393.

*Primary Examiner*—Brenda Coleman
(74) *Attorney, Agent, or Firm*—Mark R. Buscher

(57) ABSTRACT

Olanzapine and salts thereof are made by a process that utilizes an N-formyl olanzapine intermediate of formula (4) or a salt thereof

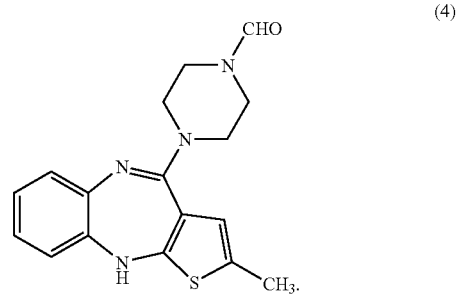

(4)

22 Claims, No Drawings

SYNTHESIS OF OLANZAPINE AND INTERMEDIATES THEREOF

This application claims the benefit of priority from U.S. Provisional Application Ser. No. 60/539,120, filed Jan. 27, 2004, and from U.S. Provisional Application Ser. No. 60/569,607, filed May 11, 2004; the entire contents of each application being incorporated herein by reference.

BACKGROUND OF THE INVENTION

The present invention relates to a method of making olanzapine including olanzapine salts, and intermediates therefor.

Olanzapine or 2-methyl-4-[4-methyl-1-piperazinyl]-10H-thieno[2,3b][1,5]-benzodiazepine is a pharmaceutically active compound that can be represented by the formula (1).

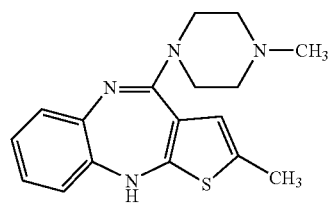

(1)

It was disclosed in EP 454436 and corresponding U.S. Pat. No. 5,229,382 as a useful antipsychotic agent. Olanzapine acts as a serotonin (5-HT2) and dopamine (D1/D2) receptor antagonist with anticholinergic activity. In commercially available final forms, the active substance is marketed as a free base, which is a white to yellow crystalline solid that is insoluble in water.

One synthetic route for making olanzapine starts from "des-methylpiperazine olanzapine precursor" of formula (3), which reacts with piperazine to form a "des-methyl olanzapine precursor" of formula (2) (see Jun-Da Cen, Chinese Journal of Pharmaceuticals 2001, 32(9),391-393). The compound (2) can be methylated to form olanzapine (see U.S. Pat. No. 4,115,568 for such suggestion). The methylation reaction can be carried out using formaldehyde under conditions of Eschweiler-Clarke reaction (see Jun-Da Cen) or by classical methylation agents such as methyl iodide (see WO 04-000847).

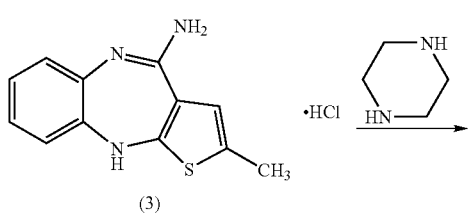

(3)

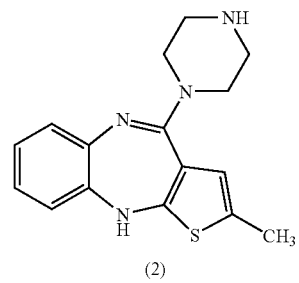

(2)

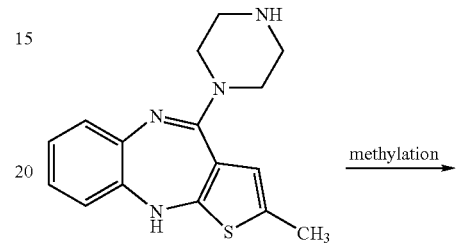

(2) methylation

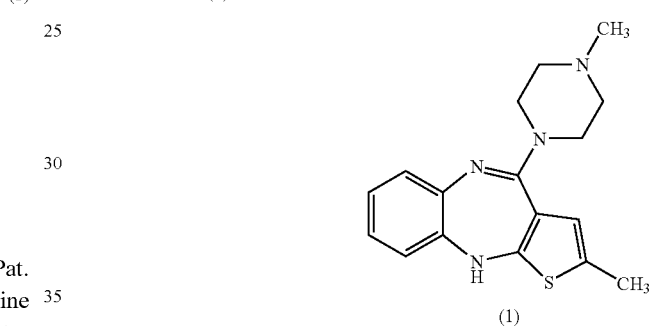

(1)

This synthetic pathway has the disadvantage that the reaction with piperazine may lead to formation of dimeric impurities and that the methylation with formaldehyde or other methylation agent may lead to side products, e.g. products of multiple methylation. All these contaminants are difficult to remove from the product. Also, methylation agents are, in general, toxic and mutagenic compounds.

An alternative of the above process was suggested in WO 04/000847 and comprises converting the compound (2) into a "formyl-olanzapine precursor" of formula (4) by a reaction with a methyl formate, and converting the compound (4) into olanzapine by a reduction with a metal borohydride.

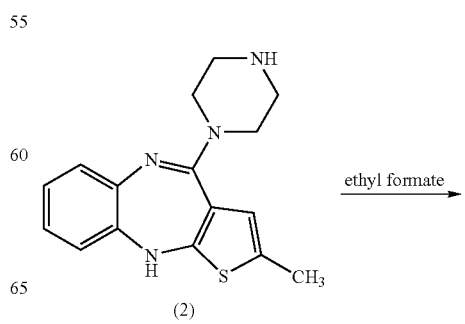

(2) ethyl formate

-continued

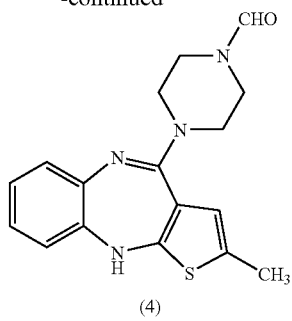

In comparison with the preceding procedure, the alternate procedure is one step longer and suffers from the same problems in the step of making compound (2). Furthermore, the reported purity of the actually obtained olanzapine product is only 88%, which is not sufficient for pharmaceutical applications.

Purifying olanzapine is generally difficult. So-called "technical grade" olanzapine, which is generally easy to form but is too impure for pharmaceutical use, has been the starting material for several attempts at forming pharmaceutically acceptable olanzapine. In general, these purification techniques, such as a crystallization, lead to irreproducible results as the formation of various olanzapine polymorphs occurs. Other techniques comprise forming a hydrate or a solvate of olanzapine and then converting the purified hydrate/solvate to olanzapine by dehydration or desolvation. But, the dehydration or desolvation usually requires treatment of the hydrate/solvate at an enhanced temperature, which may cause formation of unwanted decomposition products and a lowering the overall purity. Furthermore, the resulted product may still be contaminated with the undesired polymorphic forms as in the case of crystallization.

It would be desirable to have a synthetic route that allowed the formation of olanzapine in a more pure form.

SUMMARY OF THE INVENTION

The present invention relates to the formation, purification and/or use of an N-formyl olanzapine. Accordingly, a first aspect of the present invention relates to a process, which comprises reacting a des-piperazine olanzapine of formula (3) or a salt thereof

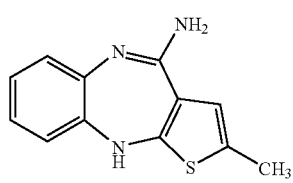

with an N-formyl piperazine of formula (5)

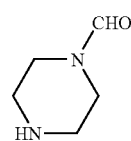

to form an N-formyl olanzapine of formula (4) or a salt thereof

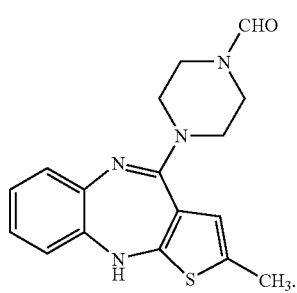

The reaction can be carried out in an inert solvent, generally a dipolar aprotic solvent, and is typically accomplished by heating. The N-formyl olanzapine can be converted to olanzapine.

Another aspect of the invention relates to a process for making an olanzapine salt, which comprises: reducing an N-formyl olanzapine of formula (4) or a salt thereof

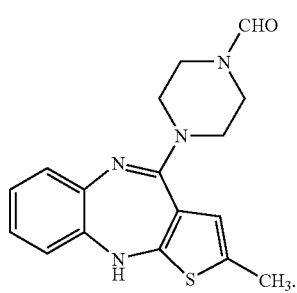

with a reducing agent in a solvent to form olanzapine or a salt thereof dissolved in said solvent; reacting said dissolved olanzapine or a salt thereof with an acid to form an acid addition salt of olanzapine; and precipitating said olanzapine acid addition salt from said solution. Precipitating the salt of olanzapine can avoid the formation of technical grade olanzapine. That is, the olanzapine salt can be obtained in a purified state and then converted to olanzapine base, if desired, in high purity.

A further aspect of the present invention relates to purifying the N-formyl olanzapine, which process which comprises:

(1) dissolving and/or slurrying an N-formyl olanzapine of formula (4)

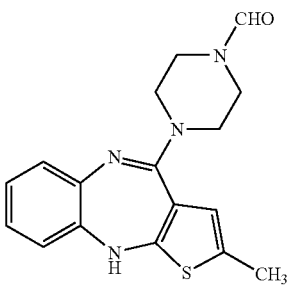

(4)

or a salt thereof in a solvent selected from the group consisting of an aliphatic alcohol, an aromatic hydrocarbon, and mixtures thereof, at a temperature of at least 35° C. to form a crystallization treatment medium;

(2) cooling said crystallization treatment medium; and (3) isolating solid N-formyl olanzapine of formula (4) having improved purity. The steps (1)-(3) can be repeated if necessary until the desired purity is reached. Generally, such a process can achieve purity of greater than 95% and preferably greater than 98%.

DETAILED DESCRIPTION OF THE INVENTION

The present invention relates to the discovery that the intermediate N-formyl olanzapine can be provided in relatively high purity and converted to olanzapine in high purity. Because N-formyl olanzapine does not suffer from the ready formation of polymorphs, in contrast to olanzapine base, it may be isolated and purified in a reliable process, easily applicable to an industrial scale. Preferred embodiments of the invention can achieve solid state olanzapine base or salt thereof in a purity of at least 98%, preferably more than 99% and more preferably more than 99.5% (calculated on an anhydrous and/or solvent-free basis). Such a pharmaceutical grade olanzapine product is suitable for being formulated into pharmaceutical compositions.

An overall synthetic scheme for making olanzapine, which combines various aspects of the present invention, is set forth below:

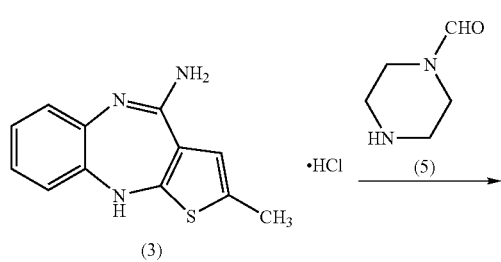

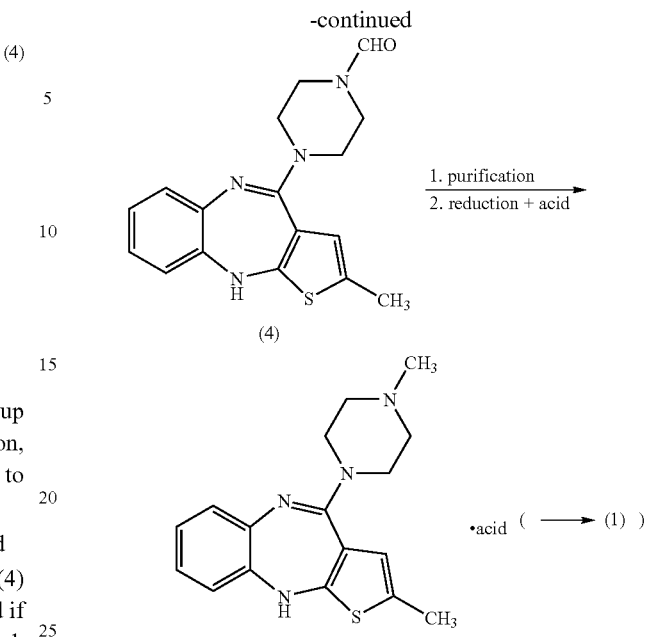

The first step reacts des-piperazine olanzapine of formula (3), shown as the HCl salt thereof in this scheme, with N-formyl piperazine (5) to produce N-formyl olanzapine (4). The starting compounds (3) and (5) are commercially available and/or readily obtained by methods known in the art. In comparison with the prior art suggestion discussed above, this represents a simplified way to obtain (4).

In general the acid addition salt (e.g. hydrochloride) of compound (3) and N-formyl piperazine (5) react together by heating in an inert solvent for a time sufficient for conversion. The conversion can be complete. The progress of the reaction, e.g., the degree of the conversion, may be monitored by a suitable method including HPLC, etc. A suitable inert solvent is generally a dipolar aprotic solvent especially a mixture of dimethyl sulfoxide and toluene. The reaction is normally carried out at elevated temperatures such as 40° C. to reflux of the solvent, and typically within 10° C. of the reflux temperature; i.e. a temperature at, or near, the reflux temperature. The reaction typically runs for 1 to 24 hours, generally 4-12 hours depending upon the scale, the temperature, the concentrations, the conversion level desired, etc. The product may be isolated in a solid state by diluting the reaction mixture with water. Ordinarily, the isolated product comprises approximately 90% of the compound (4), i.e. the product is obtainable in approx. 90% quality.

The next step shown in the overall reaction scheme involves purifying the compound (4). The crude N-formyl-olanzapine (4) is purified by crystallization from a solvent selected from the group consisting of a lower aliphatic alcohol, e.g., a C1-C4 alcohol such as methanol, or an aromatic hydrocarbon, e.g., a benzene substituted by 0-2 methyl groups such as toluene. It is not strictly required that the N-formyl olanzapine is fully dissolved in the solvent system within the crystallization. Thorough slurrying in the solvent at an elevated temperature is sufficient. In any case, heating the N-formyl olanzapine (4) in the solvent to achieve dissolution or slurrying, or both, creates the crystallization treatment medium. By subjecting the compound (4) to the crystallization treatment medium for a sufficient time, followed by cooling and isolating the solid, provides for (4) in improved purity. While not wishing to be bound by theory, it is believed that when the crude N-formyl olanzapine is not fully dissolved in the heated solvent, as in classical crystallization, at least a portion of the compound is dissolving and crystallizing. As different portions of the initially crude N-formyl olanzapine dissolve and recrystallized during the heated solvent treating, the purity of the solid N-formyl olanzapine improves. The heating is generally above 35° C. and typically in the range of 40° C. to 65° C. The time of the treatment in the crystallization treatment medium depends upon how much, if any, of the N-formyl olanzapine remains undissolved. Once the fully dissolved, the cooling can begin immediately if desired. If a slurry is made without ever reaching complete dissolution, the treatment time is generally at least one hour and typically one to four hours, but is not limited thereto. After cooling the purified solid (4) is isolated generally by filtration or centrifugation.

Generally, a compound with purity of at least 95% may be obtained with a single crystallization as described above. If not, the process of (1) dissolving and/or slurrying in the heated solvent; (2) cooling; and (3) isolating the solid N-formyl olanzapine (4) may be repeated, using the same or different conditions. Similarly, if a higher purity is desired, such as at least 98% pure, the steps can be repeated as often as necessary, using the same or different conditions.

While shown in the context of the overall scheme, it should be understood that the purification procedure can be applied to N-formyl olanzapine (4) regardless of how it was made. For example, the above-described purification technique can be applied to the N-formyl olanzapine process suggested in WO 2004/000847.

In the next step, the compound (4), or its salt, is converted to olanzapine or a salt thereof. Any technique or scheme that results in olanzapine is intended to be included within the meaning of "converting." In particular, the conditions suggested in WO 2004/000847 can be used, especially if the compound (4) has been purified. In general the conversion involves reducing the compound (4) with a reducing agent. This reduction is normally carried out in a solvent. The olanzapine base is generally formed in the solution, i.e. it normally does not precipitate out upon formation.

One particular embodiment comprises reducing the compound (4) in an olanzapine-soluble solvent with a reducing agent selected from an aluminum hydride or hydrogen in the presence of a hydrogenation catalyst, to form a solution of olanzapine. The olanzapine-soluble solvent is normally a water immiscible inert organic solvent such as an aromatic hydrocarbon, especially toluene. The reducing agent is typically an organic aluminum hydride reductant which is soluble in the olanzapine-soluble solvent such as sodium dihydro-bis(2-methoxyethoxy)aluminate, which is available commercially as RED-Al™. The side products may be removed by extracting the reaction mixture with water and with a water immiscible organic solvent, e.g. with water/ethylacetate mixture, whereby the product is preferentially concentrated in the organic layer. The so provided olanzapine solution may be further purified, if desirable, e.g. by treating with surface active material such as activated carbon.

Conveniently the solution of olanzapine, e.g., the organic layer, whether extracted or not, is subsequently treated with an acid to precipitate an olanzapine salt. Alternatively, the solution of olanzapine can be formed in the presence of an acid to form the acid addition salt in essentially a single step. The salt of olanzapine may precipitate immediately or upon cooling or other manipulation for facilitating precipitation of a compound from a solution. Almost no loss of quality has been observed in comparison with the starting material of compound (4). The acid can be organic or inorganic as long as it can form an isolatable solid salt with olanzapine. A variety of olanzapine acid addition salts have been disclosed in U.S. provisional application Ser. No. 60/539,120, filed Jan. 27, 2004, and 60/569,607, filed May 11, 2004. All of the salts disclosed therein as forming a solid salt of olanzapine are useful in the present invention for isolating olanzapine. The entire contents of each provisional application, and especially as it regards olanzapine salts, their formation, and use in purification of olanzapine, is incorporated herein by reference. The acid is preferably selected from malonic acid, glycolic acid, maleic acid, acetic acid, or benzoic acid. By isolating olanzapine as a salt, the purity of the olanzapine is maintained or enhanced. If a further improvement of quality is desirable, the olanzapine salts may be purified by an ordinary crystallization from a suitable solvent. In this way, olanzapine salts of pharmaceutical grade purity can be obtained.

Olanzapine salts made by the process of the present invention are pharmaceutically useful products and may be formulated into pharmaceutical compositions with pharmaceutical excipients.

Alternatively, the olanzapine salts produced by the process of the invention can be converted to olanzapine base and are thus suitable intermediates for making solid olanzapine base in any of its anhydrated, hydrated or solvated forms. Advantageously, the use of an olanzapine salt as an intermediate for making solid olanzapine base can avoid the formation of the problematic technical grade olanzapine. Instead, a pharmaceutical grade salt of olanzapine is formed, such as by recrystallization(s), and then converted to solid olanzapine base. In a general conversion process, the salt is treated with a suitable alkali in a suitable solvent to liberate olanzapine base. Water soluble salts may be neutralized by a suitable alkali in an aqueous environment. Water insoluble salts may be converted to olanzapine in ethanol by neutralization with the alkali. The salt of the alkali formed during the reaction is filtered off, and the olanzapine is crystallized from the solvent.

In a particular process, water hydrolysable olanzapine salts, such as olanzapine glycolate, are treated just by water, without the need of the alkali.

In another conversion process, olanzapine acetate may be converted to olanzapine Form I by heat treatment as is described more fully in U.S. provisional application Ser. No. 60/562,225, filed Apr. 15, 2004, the entire contents of which are incorporated herein by reference.

The present invention is more particularly described and explained by the following examples. It is to be understood, however, that the present invention is not limited to these examples and various changes and modifications may be made without departing from the scope of the present invention.

EXAMPLES

Example 1

N-Formyl Olanzapine (4)

In a 1000 ml flask, a mixture of 12.0 g of "des-methylpiperazine olanzapine precursor" (compound of formula (2)) hydrochloride and 40 ml of N-formyl piperazine in a mixture of 60 ml of dimethylsulfoxide and 60 ml of toluene was heated at reflux under a nitrogen atmosphere overnight. Progress was monitored by HPLC. After cooling to 40° C., 160 ml of water was added. The resulting mixture was cooled and stirred at 0° C. The solid material was isolated by filtration and washed with 2×40 ml of water. Wet solid was dried overnight at ambient conditions and subsequently at 40° C. under vacuum.

Isolated yield: 12.19 gram, Purity (HPLC): 91.6%

Example 2

Crystallization of the Compound (4)

8.0 g of crude N-formyl olanzapine precursor (compound (4)) of a purity of about 89% (HPLC) was suspended in 50 ml of methanol and heated at 60° C. for 3 hours. The hot suspension was allowed to cool to room temperature and was subsequently cooled to 5° C. under stirring. The solid material was isolated by filtration, washed with 5 ml of cold methanol and 10 ml of cold diethyl ether and dried overnight at 40° C. under vacuum.

Yield: 3.97 g, purity 96.7% (HPLC)

Example 3

Olanzapine Benzoate

In a 250 ml flask, 3.0 g of N-formyl olanzapine precursor (compound(4)) was suspended in 45 ml of dry toluene and cooled to 0° C. Under nitrogen atmosphere, 5.4 ml of Red-Al™ solution (70 wt % solution of sodium dihydrobis(2-methoxyethoxy)aluminate in toluene) was added dropwise under stirring. The resulting mixture was allowed to warm up to room temperature. Then, next 5.0 ml of Red-Al™ solution was added dropwise at this temperature. After stirring for 5 hours at room temperature, the reaction mixture was poured into 100 ml of water and immediately 100 ml of ethyl acetate was added. The mixture was filtered over a P3-filter to remove insoluble material. The biphasic filtrate was allowed to stand for separating the layers and the aqueous layer was removed and washed with 2×50 ml of ethyl acetate. The combined organic layers were washed with 2×50 ml of water, dried over anhydrous sodium sulfate and concentrated at reduced pressure to a volume of about 50-60 ml. Then, 1.12 g of benzoic acid was added in one portion and the resulting mixture was stirred at 4° C. for 4 hours. The formed solid was isolated by filtration, washed with 5 ml of cold ethyl acetate and 10 ml of cold diethyl ether, and dried overnight at 40° C. under vacuum.

Yield: 2.75 gram, purity (HPLC): 94.8%.

All of the patents mentioned above are incorporated herein by reference in their entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A process, which comprises reacting a des-piperazine olanzapine of formula (3) or a salt thereof

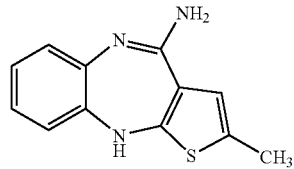

(3)

with an N-formyl piperazine of formula (5)

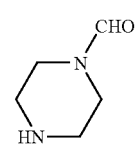

(5)

to form an N-formyl olanzapine of formula (4) or a salt thereof

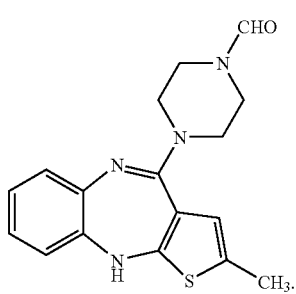

(4)

2. The process according to claim 1, wherein said reaction is carried out in a dipolar aprotic solvent.

3. The process according to claim 2, wherein said solvent is a mixture of dimethyl sulfoxide and toluene.

4. The process according to claim 2, wherein said reaction is carried out at a temperature within the range of 40° C. up to the reflux temperature.

5. The process according to claim 1, which further comprises isolating and purifying said N-formyl olanzapine of formula (4) to a purity of at least 95%.

6. The process according to claim 5, wherein said purifying comprises:
   (1) dissolving and/or slurrying said N-formyl olanzapine of formula (4) in a solvent selected from the group consisting of an aliphatic alcohol, an aromatic hydrocarbon, and mixtures thereof, at a temperature of at least 35° C. to form a crystallization treatment medium;
   (2) cooling said crystallization treatment medium;
   (3) isolating solid N-formyl olanzapine of formula (4) having improved purity; and optionally
   (4) repeating steps (1)-(3).

7. The process according to claim 6, wherein said crystallization treatment medium is heated to a temperature of 40° C. to 65° C.

8. The process according to claim 6, wherein said crystallization treatment medium is maintained in a heated condition for at least 1 hour.

9. The process according to claim 7, wherein said crystallization treatment medium is maintained in a heated condition for 1-4 hours.

10. The process according to claim 6, wherein said N-formyl olanzapine is purified to a purity of at least 98%.

11. The process according to claim 1, which further comprises converting said N-formyl olanzapine of formula (4) to form olanzapine or a salt thereof.

12. The process according to claim 11, wherein said converting comprises reducing said N-formyl olanzapine of formula (4) in an olanzapine-soluble solvent with a reducing agent selected from an aluminum hydride or hydrogen in the presence of a hydrogenation catalyst, to form a solution of olanzapine or a salt thereof.

13. The process according to claim 12, wherein said reducing agent is a sodium dihydro-bis(2-methoxyethoxy) aluminate.

14. The process according to claim 12, wherein said olanzapine-soluble solvent is an aromatic hydrocarbon.

15. The process according to claim 14, wherein said olanzapine-soluble solvent is toluene.

16. The process according to claim 12, which further comprises reacting said solution of olanzapine or a salt thereof with an acid and precipitating an olanzapine acid addition salt from said solution of olanzapine.

17. The process according to claim 16, wherein said acid is selected from the group consisting of malonic acid, glycolic acid, maleic acid, benzoic acid, and acetic acid.

18. The process according to claim 16, which further comprises converting said olanzapine acid addition salt to olanzapine base.

19. A process for making an olanzapine salt, which comprises:
    reducing an N-formyl olanzapine of formula (4) or a salt thereof

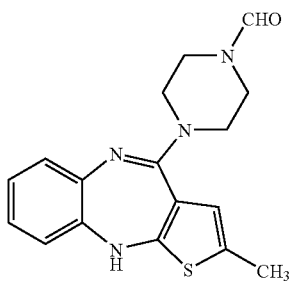

(4)

with a reducing agent in a solvent to form olanzapine or a salt thereof dissolved in said solvent;

reacting said dissolved olanzapine or a salt thereof with an acid to form an acid addition salt of olanzapine; and precipitating said olanzapine acid addition salt from said solution.

20. The process according to claim 19, wherein said reduction is carried out in toluene and said reducing agent is a sodium dihydro-bis(2-methoxyethoxy)aluminate.

21. A process which comprises:
    (1) dissolving and/or slurrying an N-formyl olanzapine of formula (4)

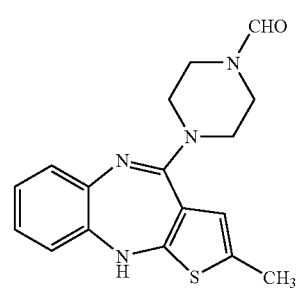

(4)

or a salt thereof in a solvent selected from the group consisting of an aliphatic alcohol, an aromatic hydrocarbon, and mixtures thereof, at a temperature of at least 35° C. to form a crystallization treatment medium;

(2) cooling said crystallization treatment medium; and (3) isolating solid N-formyl olanzapine of formula (4) having improved purity.

22. The process according to claim 21, which further comprises converting said N-formyl olanzapine of formula (4) having improved purity into olanzapine.

* * * * *